(12) United States Patent
Jensen et al.

(10) Patent No.: US 7,542,790 B2
(45) Date of Patent: Jun. 2, 2009

(54) APPARATUS AND METHOD FOR VELOCITY ESTIMATION IN SYNTHETIC APERTURE IMAGING

(75) Inventors: Jorgen Arendt Jensen, Horsholm (DK); Svetoslav Nikolov, Farum (DK)

(73) Assignee: B-K Medical A/S, Gentoft (DK)

( * ) Notice: Subject to any disclaimer, the term of this patent is extended or adjusted under 35 U.S.C. 154(b) by 315 days.

(21) Appl. No.: 10/491,170

(22) PCT Filed: Oct. 1, 2002

(86) PCT No.: PCT/DK02/00648

§ 371 (c)(1), (2), (4) Date: Oct. 4, 2004

(87) PCT Pub. No.: WO03/029840

PCT Pub. Date: Apr. 10, 2003

(65) Prior Publication Data

US 2005/0043622 A1    Feb. 24, 2005

(30) Foreign Application Priority Data

Oct. 2, 2001    (EP) .................................. 01610104

(51) Int. Cl.
*A61B 5/05* (2006.01)
*A61B 8/00* (2006.01)
*A61B 8/12* (2006.01)
*A61B 8/14* (2006.01)

(52) U.S. Cl. ........................ 600/407; 600/437; 600/443

(58) Field of Classification Search ................. 600/443, 600/437; 324/76.49; 702/33, 39; 73/584, 73/587, 596, 597, 620, 627, 628, 632, 633
See application file for complete search history.

(56) References Cited

U.S. PATENT DOCUMENTS

| 5,465,722 A | * | 11/1995 | Fort et al. .................... 600/447 |
| 5,531,117 A | * | 7/1996 | Fortes .......................... 73/602 |
| 5,769,079 A | * | 6/1998 | Hossack ..................... 600/454 |
| 6,689,063 B1 | * | 2/2004 | Jensen et al. ................. 600/443 |

FOREIGN PATENT DOCUMENTS

WO     WO 00/68931    * 11/2000

OTHER PUBLICATIONS

J. T. Ylitalo, "In-vitro study of computed ultrasound imaging method." In Proc. IEEE Ultrason. Symp., pp. 1577-1580, 1994.

(Continued)

*Primary Examiner*—Ruth S Smith
*Assistant Examiner*—James Kish
(74) *Attorney, Agent, or Firm*—Finnegan, Henderson, Farabow, Garrett & Dunner, L.L.P.

(57) ABSTRACT

The invention relates to an apparatus for flow estimation using synthetic aperture imaging. The method uses a Synthetic Transmit Aperture, but unlike previous approaches a new frame is created after every pulse emission. In receive mode parallel beam forming is implemented. The beam formed RF data is added to the previously created RF lines obtained by the same transmit sequence. The apparatus comprises a pulser (1) to generate a pulsed voltage signal, that is fed to the emit beam former (2). The emit beam former (2) is connected to the emitting transducer array (3). The ultrasound is reflected by the object (4) and received by the elements of the transducer array (5). All of these signals are then combined in the beam processor (6) to focus all of the beams in the image in both transmit and receive mode and the simultaneously focused signals are used for updating the image in the processor (7). The estimation processor (8) to correlate the individual measurements to obtain the displacement between high-resolution images and thereby determine the velocity.

15 Claims, 6 Drawing Sheets

OTHER PUBLICATIONS

J. T. Ylitalo and H. Ermert, "Ultrasound synthetic aperture imaging: monostatic approach." IEEE Trans. Ultrason., Ferroelec., Freq. Contr., 41:333-339, 1994.

J. T. Ylitalo, "Synthetic aperture ultrasound imaging using a convex array." In. Proc. IEEE Ultrason. Symp., pp. 1337-1340, 1995.

J. T. Ylitalo, "A fast ultrasonic synthetic aperture imaging method: application to NDT." Ultrasonics, pp. 331-333, 1996.

J. T. Ylitalo, "On the signal-to-noise ratio of a synthetic aperture ultrasound imaging method." Eur. J. Ultrasound, pp. 227-281, 1996.

M. Karaman, P. C. Li, and M. O'Donnell, "Synthetic aperture imaging for a small scale systems." IEEE Trans. Ultrason., Ferroelec., Freq. Contr., 42:429-442, 1995.

R. Y. Chiao and L. J. Thomas, "Analytic evaluation of sampled aperture ultrasonic imaging techniques for NDE." IEEE Trans. Ultrason., Ferroelec., Freq. Contr., 41:484-493, 1994.

S. Holm and H. Yao, "Improved framerate with synthetic transmit aperture imaging using prefocused subapertures." Proc. IEEE Ultrason. Symp., pp. 1535-1538, 1997.

G. R. Lockwood, J. R. Talman, and S. S. Brunke, "Real-time 3-D ultrasound imaging using sparse synthetic aperture beamforming." IEEE Trans. Ultrason., Ferroelec., Freq. Contr., 45:980-988, 1998.

C. R. Hazard and G. R. Lockwood, "Theoretical assessment of a synthetic aperture beamformer for real-time 3-D imaging." IEEE Trans. Ultrason., Ferroelec., Freq. Contr., 46:972-980, 1999.

S. I. Nikolov., K. Gammelmark, and J. A. Jensen, "Recursive ultrasound imaging." Proc. IEEE Ultrason. Symp., vol. 2, pp. 1621-1625, 1999.

L. F. Nock and G. E. Trahey, "Synthetic receive aperture imaging with phase correction for motion and for tissue inhomogenities—part II: effects of and correction for motion." IEEE Trans. Ultrason., Ferroelec., Freq., Contr., 39:496-501, 1992.

H. S. Bilge, M. Karaman, and M. O'Donnell, "Motion estimation using common spatial frequencies in synthetic aperture imaging." In Proc. IEEE Ultrason. Symp., pp. 1551-1554, 1996.

S. G. Foster, P. M. Embree, and W. D. O'Brien, "Flow velocity profile via time-domain correlation: Error analysis and computer simulation." IEEE Trans. Ultrason., Ferroelec., Freq. Contr, 37:164-175, 1990.

S. I. Nikolov, K. Gammelmark, and J. A. Jensen, "Velocity estimation using recursive ultrasound imaging and spatially encoded signals." In Proc. IEEE Ultrason. Symp., vol. 2, pp. 1473-1477, 2000.

J. A. Jensen, "Estimation of Blood Velocities Using Ultrasound: A Signal Processing Approach." Cambridge University Press, New York, 1996.

J. A. Jensen, "Stationary echo canceling in velocity estimation by time-domain cross-correlation," IEEE Trans. Med. Imag., 12:471-477, 1993b.

C. Kasai, K. Namekawa, A. Koyano, and R. Omoto, "Real-time two-dimensional blood flow imaging using an autocorrelation technique." IEEE Trans. Son. Ultrason., 32:458-463, 1985.

K. W. Ferrara and V. R. Algazi, "Estimation of blood velocity using the wideband maximum likelihood estimator." Proc. IEEE Ultrason. Symp., pp. 897-901, 1989.

O.Bonnefous, "Measurement of the complete 3D velocity vector of blood flows." Proc. IEEE Ultrason. Symp., pp. 795-799, 1988.

J. A. Jensen and I. R. Lacasa, "Estimation of blood velocity vectors using transverse ultrasound beam focusing and cross-correlation." Proc. IEEE Ultrason. Symp., pp. 1493-1497, 1999.

I. R. Lacasa, "Estimation of blood velocities with ultrasound." Master's thesis, Department of Information Technology, Technical University of Denmark, 1999.

J. A. Jensen and P. Gori, "Improved accuracy in the estimation of blood velocity vectors using matched filtering." Proc. IEEE Ultrason. Symp., vol. 2, pp. 1525-1530, 2000.

P. Munk, "Estimation of blood velocity vectors using ultrasound." PhD thesis, Department of Information Technology, Technical University of Demark, Lyngby, Demark, 2000.

J. A. Jensen and P. Munk, "A new method for estimation of velocity vectors." IEEE Trans. Ultrason., Ferroelec., Freq. Contr., 45:837-851, 1998.

J. A. Jensen, "A new estimator for vector velocity estimation." IEEE Trans. Ultrason., Ferroelec., Freq. Contr., 48(4): 886-894, 2001.

G. E. Trahey, J. W. Allison, and O. T. Von Ramm, "Angle independent ultrasonic detection of blood flow." IEEE Trans. Biomed. Eng., BME-34:965-967, 1987.

G. E. Trahey, S. M. Hubbard, and O. T. Von Ramm, "Angle independent ultrasonic blood flow detection by frame-to-frame correlation of B-mode images." Ultrasonics, 26:271-276, 1988.

L. N. Bohs and G. E. Trahey, "A novel method for angle independent ultrasonic imaging of blood flow and tissue motion." IEEE Trans. Biomed. Eng., 38:280-286, 1991.

L. N. Bohs, B. J. Geiman, K. R. Nightingale, C. D. Choi, B. H. Friemel, and G. E. Trahey, "Ensemble tracking: a new method for 2D vector velocity measurement." Proc. IEEE Ultrason. Symp., pp. 1485-1488, 1995.

B. Geiman, L. Bohs, M. Anderson, and G. E. Trahey, "Initial experimental results using ensemble tracking for 2D vector velocity measurement." Proc. IEEE Ultrason. Symp., pp. 1241-1244, 1996.

L. N. Bohs, B. J. Geiman, S. M. Breit, and G. E. Trahey, "Ensemble tracking for 2D vector velocity measurement: experimental and initial clinical results," IEEE Trans. Ultrason., Ferroelec., Freq. Contr., 45:912-924, 1998.

\* cited by examiner

APPARATUS AND METHOD FOR VELOCITY ESTIMATION IN SYNTHETIC APERTURE IMAGING

FIELD OF THE INVENTION

The invention relates to an apparatus and a method for determining the velocity of a remotely sensed object using wave energy such as sound, in particular ultrasound, or electromagnetic radiation. A synthetic aperture imaging techniques, where the received signals for a number of transmissions are grouped to form similar but spatially shifted images, is used to determine movement of the object, in particular blood flow. By using a number of pulse emissions, the interpulse movement can be estimated and the velocity found from the estimated movement and the time between pulses. The invention is based on the principle of using a synthetic aperture imaging over a number of emissions and then group the focused data to make the correlation between the focused and displaced images high in order to optimize the velocity estimation process.

BACKGROUND OF THE INVENTION

The use of synthetic transmit aperture ultrasound imaging (STAU) for tissue imaging has been considered for some time [1, 2, 3, 4, 5, 6]. It has not been in clinical use because of the relatively higher complexity of the hardware and because of its inability to estimate blood velocities. One of the requirements for estimating the flow is to have RF data acquired in the same direction at high pulse repetition frequencies. The synthetic aperture algorithms acquire the data for a single RF line over a number of emissions. The fastest approach to acquire data is the synthetic transmit aperture acquisition [7, 8, 9, 10]. Even so, at least two emissions are necessary to beam form the data, and the beam formation is then on data that are displaced relative to each other.

A beam forming method allowing for a new image to be created at every emission has previously been suggested [11]. This method overcomes the first limitation of the synthetic aperture imaging, as there is a scan line at every emission for every direction. This allows for a whole flow map to be created at every emission. The data, however, still suffers from motion artifacts.

Previous attempts have been confined to the estimation of gross tissue motion for motion compensation [12, 13]. The approach suggested by Nock and Trahey [12] uses cross-correlation between the received raw RF signals. The algorithm, however, relies on the fact the transmission is focused, and that the received signals come from the same direction. It is therefore not suitable for STAU. The method suggested by Bilge et al. [13] relies on the cross-correlation between low-resolution images, which are formed using the same transmit-receive pairs of transducer elements. The beam is, however, broad and the blood cells within its limits have a wide spread of velocities. This results in an increased bias and uncertainty of the estimates.

Both types of motion compensation schemes show higher performance when the images were obtained using the same transmit/receive element pairs, or in other words have the same spatial frequencies. The high-resolution images (HRI) have the highest overlap of spatial frequencies, and therefore they should give the best estimates. The correlation of the signals received from the blood cells decreases rapidly due to migration of scatterers, beam-width modulation, and flow gradients (change in the relative positions between the scatterers) [14]. The HRIs must be generated after every emission, which is possible using recursive ultrasound imaging. These images suffer from motion artifacts, which changes from frame to frame. In [15] it was shown that it is possible to both compensate for motion artifacts and estimate the velocity from the motion-compensated HRIs. The success of the velocity estimation relies on the success of the motion compensation, which makes the whole approach unstable. The purpose of the method suggested is to avoid motion compensation prior to velocity estimation.

SUMMARY OF THE INVENTION

It is the object of the invention to overcome the above-mentioned deficiencies and disadvantages of the known methods and apparatuses. With the invention this object is achieved by an apparatus that uses a combination of the obtained measurements, so that motion compensation is avoided. This is done by introducing a modified cross-correlation estimator making it possible to estimate the velocity from the non motion-compensated high-resolution images.

BRIEF DESCRIPTION OF THE DRAWINGS

The invention will be described in detail hereinafter with reference to the accompanying drawings.

SYNTHETIC APERTURE DATA ACQUISITION AND IMAGE FORMATION

Figure 1:
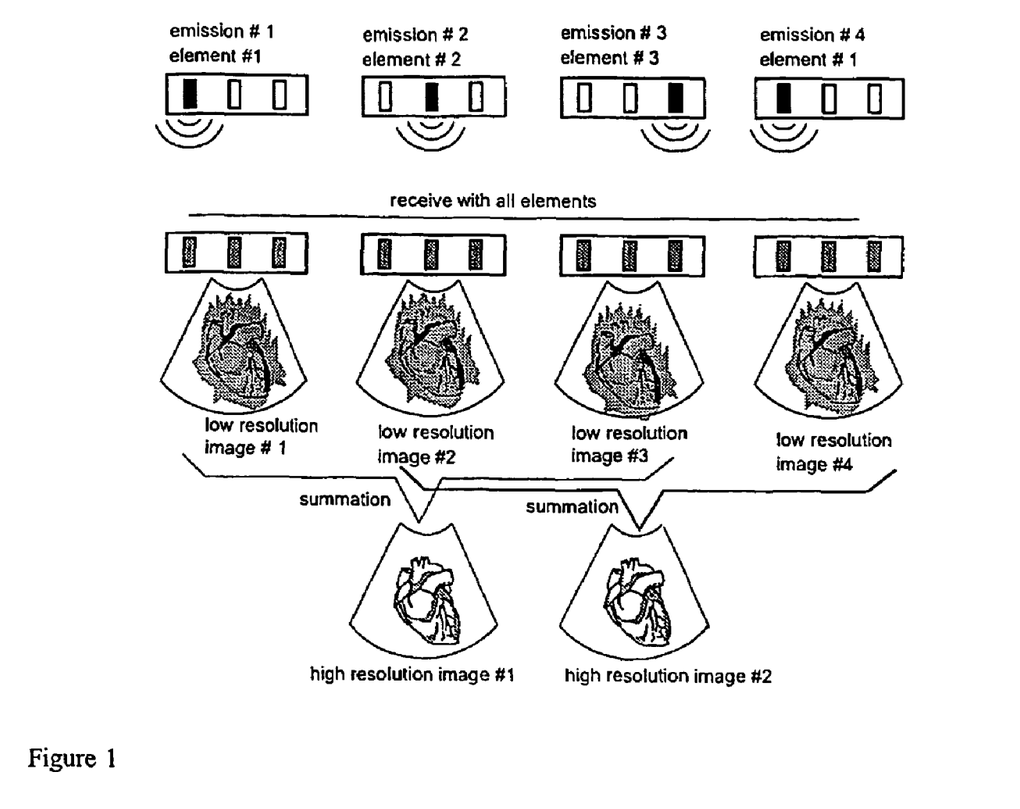
FIG. 1 illustrates how synthetic transmit aperture imaging is performed. The array consists of 3 elements. The figure shows 4 consecutive emissions. Two high-resolution images are created: one at emission # 3 and one at emission # 4.

The generation of synthetic aperture images and recursive imaging will be reviewed here. Consider the imaging situation shown in FIG. 1. The depicted transducer has N=3 elements. In normal synthetic transmit aperture, the transducer fires N=3 times, using a single element $i \in [1, 3]$ in transmission. At every emission a low-resolution image $LRI_i$ is created. Summing the low-resolution images coherently, a high-resolution image $HRI_i$ is created. After the high-resolution image is created, all the information is discarded and the process is repeated all over again.

If the medium is stationary the order in which the elements transmit does not matter. In other words, whether the order of transmission was {{i=1}, {i=2}, {i=3}} or {{i=2}, {i=3}, {i=1}} the result of summing the low-resolution images would yield the same high-resolution one. Going back to FIG. 1 it can be seen that a high-resolution image can be created at emission i=3, combining the low-resolution images from $LRI_1$ to $LRI_3$, which were obtained by exciting the consecutively the elements from 1 to 3. Low-resolution image $LRI_4$ was obtained by transmitting again with element # 1. Hence, combining low-resolution images from $LRI_2$ to $LRI_4$ (i ∈ [{2}, {3}, {1}]), a new high-resolution one can be created at emission # 4.

An index of the emissions n\in [1, ∝) is introduced, which counts the emissions from time zero. From FIG. 1 it can be seen that emission # 4, is done again with element # 1. The relation between the emission number n and the index of the transmitting element i is given by $$i=((n-1) \bmod N)+1 \tag{1}$$

The same element i is used at emissions n, n−N and n+N:

$$\begin{aligned} i &= ((n-1) \bmod N) + 1 \\ &= ((n-N-1) \bmod N) + 1 \\ &= ((n+N-1) \bmod N) + 1 \end{aligned} \tag{2}$$

The signal received by element j after transmitting with element i is denoted as $r_{ij}(t)$. Thus, the low-resolution scan line $L^{(n)}(t)$ obtained after emitting with element i is expressed as:

$$L^{(N)}(t) = \sum_{j=1}^{N} w_{ij}(t) r_{ij}(t - \tau_{ij}(t)) \tag{3}$$

where $w_{ij}(t)$ is a dynamic apodization coefficient, and $\tau_{ij}(t)$ is a delay dependent on the transmitting element i, on the receiving element j, and on the current focal point. For simplicity the time dependence of the delay and the apodization coefficient will be omitted for ease of notation.

The signal at emission n received by element j is $r_{n;j}(t)$. This is an alternative notation for $r^{ij}(t)$, which exploits the relation between n, and j. In other words:

$$r_{ij}(t) \equiv r_{n;j}(t)$$

$$i=((n-1) \bmod N)+1$$

The beam formation of a single low-resolution scan-line $L^{(n)}$ (t) is then:

$$L^{(n)}(t) = \Sigma w_{ij} r_{n;j}(t - \tau_{ij}) \tag{4}$$

Assuming stationary tissue, the signal received by element j after transmitting with element i will be the same, regardless of the emission number. The following equation is therefore valid:

$$r_{n;j}(t) = r_{n+kN;j}(t), \text{ where } k=0, \pm 1, \pm 2, \tag{5}$$

Lines in the low-resolution images obtained at emissions n and n+kN are therefore the same, provided that the imaged tissue is stationary:

$$L^{(n)}(t) = \sum_{j=1}^{N} w_{ij} r_{n;j}(t - \tau_{ij}) \tag{6}$$

$$L^{(n+kN)}(t) = \sum_{j=1}^{N} w_{ij} r_{n+kN;j}(t - \tau_{ij}) \tag{7}$$

$$r_{n+kN;j}(t) = r_{n;j}(t) \tag{8}$$
$$\Downarrow$$
$$L^{(n)}(t) = L^{(n+kN)}(t) \tag{9}$$

The order in which the transducer elements emit does not matter. Two high-resolution images at two consecutive emissions can be beam formed as follows:

$$H^{(n)}(t) = \sum_{k=n-N+1}^{n} L^{(k)}(t) \tag{10}$$

$$H^{(n-1)}(t) = \sum_{k=n-N}^{n-1} L^{(k)}(t) \tag{11}$$

Subtracting $L^{n-1}(t)$ from $L^{(n)}(t)$ gives:

$$H^{(n)}(t) = H^{(n-1)}(t) + L^{(n)}(t) - L^{(n-N)}(t) \tag{12}$$

This gives a recursive formula for creating a high-resolution image from the previous high-resolution one.

Flow cannot be estimated by using the beam formed lines from successive images generated in this way. The reason is that the image gets distorted, and the distortion is different from frame to frame depending on the position of the transmitting element. The standard estimators cannot be directly applied motion compensation must be done as suggested in [15]. The makes the beam formation depend on the motion, which has to be estimated from the beam formed data leading to an unstable imaging situation.

Measurement Principle

Figure 2:
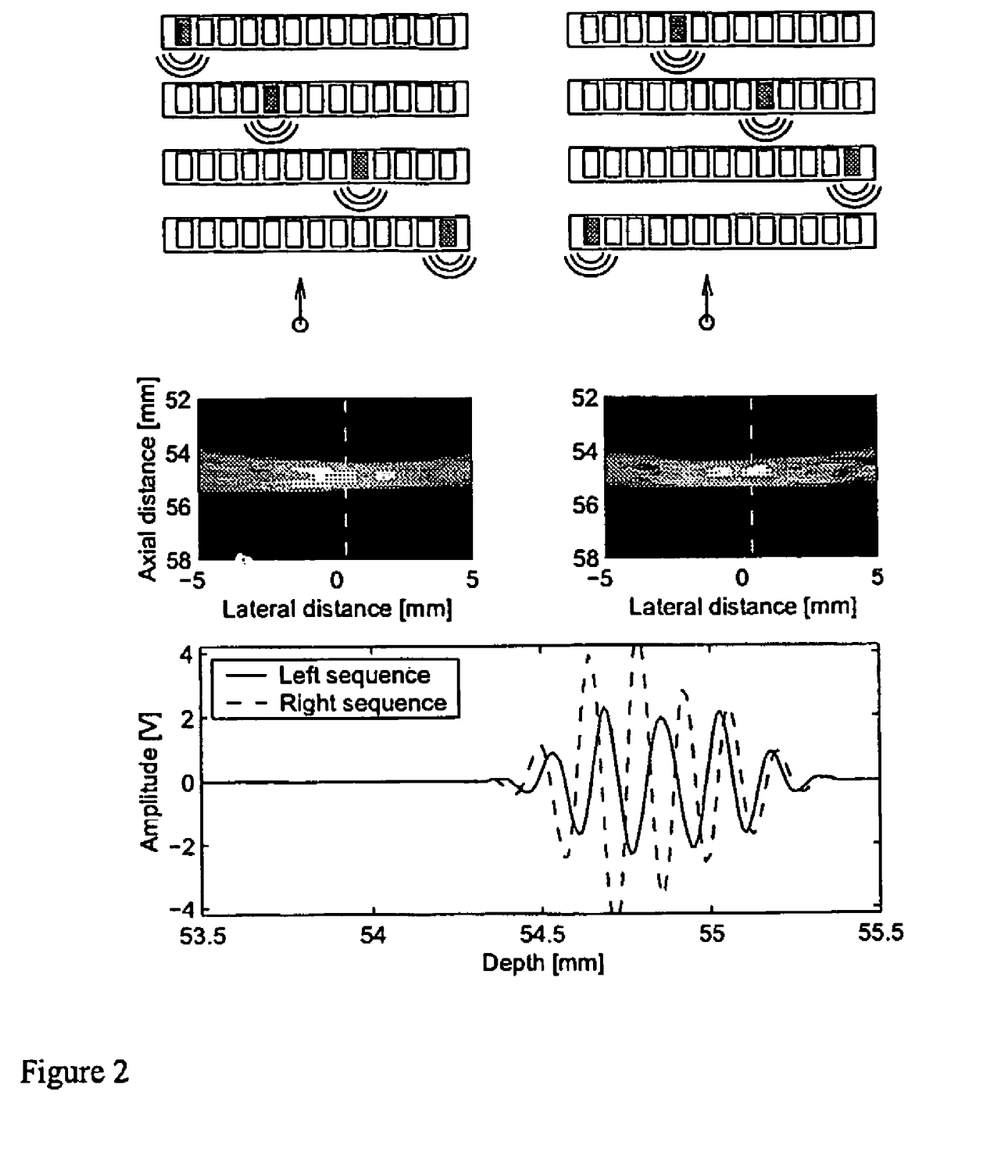
FIG. 2 shows the point spread functions obtained using different transmit sequences.

Consider the simple experiment simulated in Field II and shown in FIG. 2. A single scatterer moves towards the transducer. The image is formed using four transmissions. Initially the scatterer is centered at 55 mm away from the transducer. Between two emissions it moves at a distance $\Delta z = -\lambda/4$. The simulated transducer has 64 elements, a center frequency of 5 MHz and a pitch of $\lambda$, with an assumed speed of sound of 1540 m/s. The left and right images are formed transmitting sequentially with elements {1, 22, 43, 64 } and {22, 43, 64, 1 }, respectively. In both cases the scatterer starts from the same position. The middle row of images in FIG. 2 shows 50 dB B-mode images of the obtained point-spread-functions. They are not symmetric and differ in shape. Comparing the two RF lines reveals that the echoes are shifted and different in shape. Because of the change in shape the cross-correlation is low and the velocity cannot be estimated with a high precision. If the synthetic aperture is to be used for velocity estimation of blood flow, one must consider the velocity gradient present in the flow, which decreases the correlation between the consecutive RF signals even more. The conclusion is that the consecutive high-resolution non-motion-compensated RF lines are not suited for velocity estimations.

The reason for this is that the motion artifacts are caused by the change of position of both the scatterer and the transmitting element. This is confirmed by FIG. 2 which shows that for the same displacement of the scatterer, and different transmit sequence the motion artifacts differ.

Velocity estimators using conventional beam formation methods compares RF signals from the same range (depth) [16]. Because the sound travels through the same tissue layers, the data samples taken at the same depth and direction have undergone the same distortions (phase aberration, refraction, shift in mean frequency, attenuation, etc.). The estimation of blood is based on comparing the changes (phase shifts) in the signal at the particular point, from which the velocity is estimated. The same principle can be applied to estimating the velocity using synthetic aperture imaging.

Figure 3:
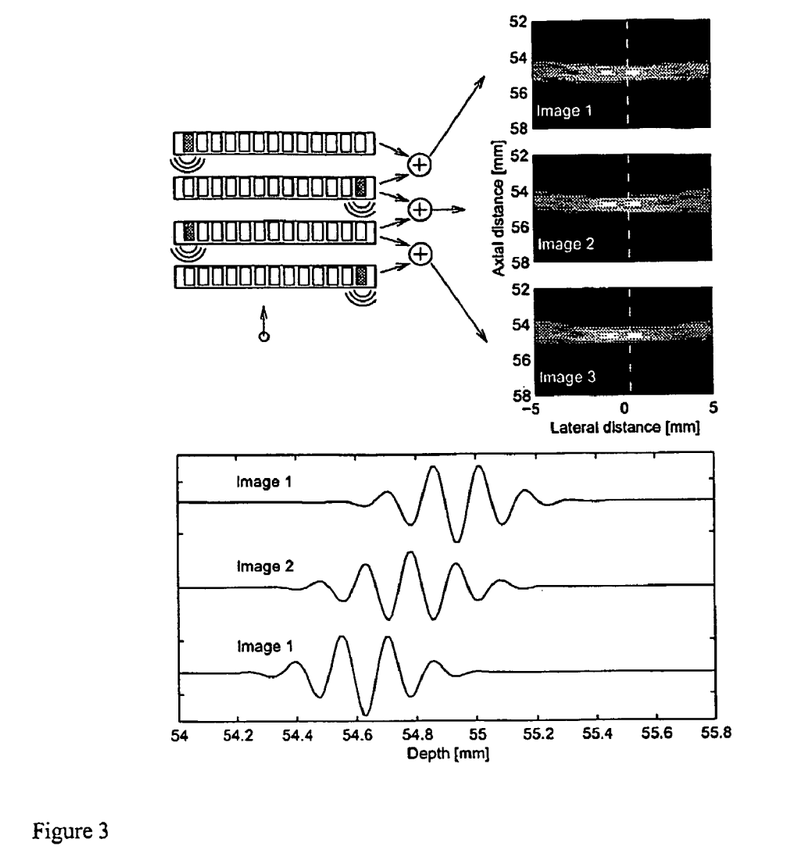
FIG. 3 shows a comparison between three high-resolution images of a moving point scatterer.

Consider FIG. 3, which shows the creation of 3 high-resolution images using two emissions per image. The transmit sequence is illustrated in the top left part of the figure. In the right side of the figure the B-mode images of the created point-spread-functions are given. It can be clearly seen that they have different geometries. The bottom plot shows a single RF line from each of the images. The RF lines from the first and the third images are time-shifted versions of each other, while the RF line from the second image has a different appearance.

Figure 4:
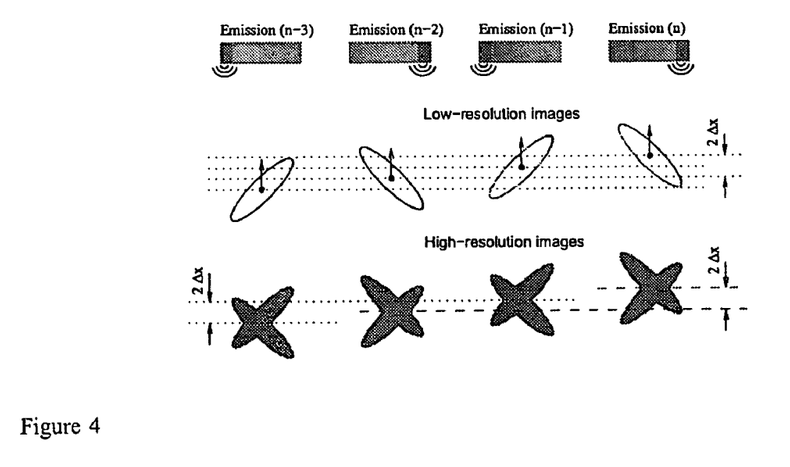
FIG. 4 illustrates the fact that images of a moving scatterer acquired at different time instances, but using the same transmit order, are translated versions of each other.

The two-dimensional point spread function PSF(x, z; $z_f$) is obtained by range-gating the beam formed RF lines from the high-resolution image around the time instance t corresponding to the image depth $z_f$. The above explanation shows that for small distances (up to several wavelengths) there is a segment in the high-resolution line $H^{(n)}(t)$, which is a time-shifted version of a segment from the high-resolution line $H^{(n-N)}(t)$:

$$H^{(n)}(t) = H^{(n-N)}(t - t_s) \quad (13)$$

where $t_s$ is the time shift between the lines given by:

$$t_s = \frac{2v_z}{c} N T_{prf} \quad (14)$$

where $v_z$ is the blood velocity along the focused line, c is the speed of sound, and $T_{prf}$ is the time between pulse emissions. The two scan lines are beam formed in the same direction and the motion is along the scan line itself as shown in FIG. 4.

The shift in position of the high-resolution images can be found from the cross-correlation function:

$$R_{n-N,n} = \frac{1}{2T} \int_T H^{(n-N)}(t) H^{(n)}(t+\tau) dt \quad (15)$$

$$= \frac{1}{2T} \int_T H^{(n-N)}(t) H^{(n-N)}(t+\tau-t_s) dt$$

$$= R_{n-N,n-N}(\tau - t_s)$$

The peak of the cross-correlation function is located at $\tau = t_s$. The velocity is then found from the time shift:

$$v = \frac{c}{2} \frac{t_s}{N T_{prf}} \quad (16)$$

Thus, the measurement principle estimates the time shifts between two high-resolution scan lines. The images from which the time shifts can be estimated must be acquired using the same transmit sequence, so they experience the same motion artifacts.

Estimation of the Cross-Correlation Function

Figure 5:
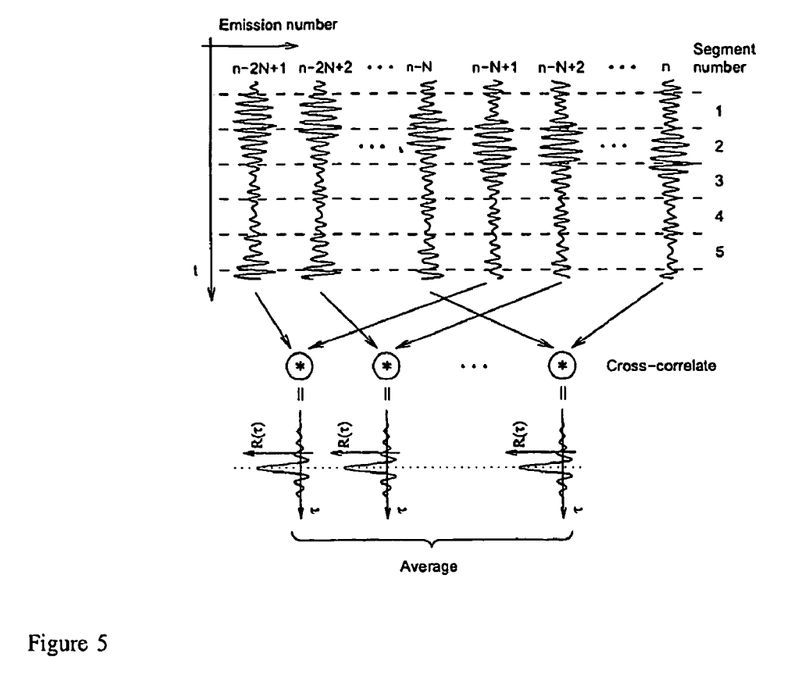
FIG. 5 shows the estimation of the cross-correlation function from a number of high-resolution RF lines.

FIG. 5 shows the process of estimating the cross-correlation function. Only a single RF line (along the same direction) from consecutive high-resolution images is shown. Two adjacent RF lines have decreased correlation due to motion artifacts caused by different transmit sequences. The same transmit sequence is used for RF lines that are separated by N-1 emissions. The RF lines are divided into segments and the segments from the same depth are cross-correlated. The discrete version of the cross-correlation is:

$$\hat{R}_{1N}[n, i_{seg}] = \frac{1}{N_s} \sum_{k=0}^{N_s-1} H^{(1)}[k + i_{seg}N_s] H^{(N)}[k + i_{seg}N_s + n] \quad (17)$$

where $N_s$ is the number of samples in the segment, and $i_{seg}$ is the number of the segment. To improve the estimate, some averaging must be done. Assuming that the velocity does not change significantly, the time shift $t_s$ estimated from $\hat{R}_{1N}$ should be the same as the time shift of the peak of the cross-correlation function $R_{2,N+1}$ as shown in FIG. 5. The averaging can be expressed as:

$$\hat{R}_{1Nd}[n, i_{seg}] = \frac{1}{N_s(N_c-1)} \sum_{i=0}^{N_c-2} \sum_{k=0}^{N_s-1} H^{(i)}[k + i_{seg}N_s] H^{(i+N)}[k + i_{seg}N_s + n] \quad (18)$$

where $N_c$ is the number of lines over which the averaging is done. If the images were created after every N emissions, then the total number of emissions needed for the velocity estimate would be $N_c N$. For N=8 and $N_c$=16, the total number of emissions would be $N_c N$=128. The correlation between the high-resolution lines would decrease due to acceleration, velocity gradients and migration of scatterers. In the new approach only $N+N_c$=24 emissions are necessary, thus preserving the high-correlation between the images and giving the possibility of estimating the flow with low bias and variance.

The velocity is found from the position of the peak in the cross-correlation function, where the sample index is denoted by $\eta_m$. The span of $\hat{R}_{12d}$ determines the maximum detectable velocity. In order to detect the same velocity range as the "conventional" cross-correlation estimator, the length of the interval in which the peak is searched must be N times bigger. If the search length is within the interval $[-N_s, N_s]$, then the largest detectable velocity becomes:

$$v_{max} = \frac{c}{2} N_s \frac{f_{prf}}{f_s} \quad (19)$$

The minimum velocity is:

$$v_{min} = \frac{c}{2N} \frac{f_{prf}}{f_s} \quad (20)$$

which is N times smaller than the minimum detectable velocity in the conventional cross-correlation estimators. The estimate's precision can be improved by fitting a second order curve to the estimate, and interpolating the time shift:

$$\eta_s = \eta_m - \frac{\hat{R}_{1Nd}[\eta_m + 1] - \hat{R}_{1Nd}[\eta_m - 1]}{2(\hat{R}_{1Nd}[\eta_m + 1] - 2\hat{R}_{1Nd}[\eta_m] + \hat{R}_{1Nd}[\eta_m - 1])} \quad (21)$$

Stationary Echo Canceling

Usually the echo canceling is done by subtracting the adjacent lines [16, 17] or by using a high-pass filter with very short impulse responses. This way of processing is chosen because of the short data sequences available for the motion, typically $N_c=8$ or 10. Using a synthetic aperture imaging with recursive beam formation gives an uninterrupted data stream and filters with long impulse responses can be used. So that both traditional echo canceling methods can be used and long FIR or IIR low pass filters.

Prospective of Velocity Estimation with Synthetic Aperture Imaging

In conventional ultrasound scanners the pulse is sent several times in the same direction in order to estimate the velocity. This leads to a decrease in the frame rate. Because of its nature, synthetic transmit aperture ultrasound imaging, or more precisely its variation recursive ultrasound imaging generates high-resolution RF lines at every emission. This gives an uninterrupted flow of data. The estimates can be based on larger data segments, thus, improving the precision of the estimates, although the estimates also can be made with only a few emissions as they are normally done in conventional systems. This opens up for the possibility to have real-time velocity estimates in real-time 3D systems, thus, making these systems full-featured ultrasound scanners.

It has been shown that in order to work with synthetic aperture imaging, the velocity estimation algorithms must be altered. The actual velocity estimation can be made with any conventional estimation algorithm that is properly altered to use the recursive synthetic aperture data. A very attractive group of estimators is the ones using time-shift measurement as described. Other algorithms can also be directly used as the autocorrelation approach by Kasai et al. [18] or maximum likelihood techniques [19].

Velocity Estimation Using Cross-Correlation along the Blood Vessel

The estimation of the velocity using cross-correlation of signals perpendicular to the ultrasound beam was first suggested by Bonnefous [20]. It was further developed to obtain signal along the velocity vector in the blood vessel by Jensen and Lacasa [21, 22].

Figure 6:
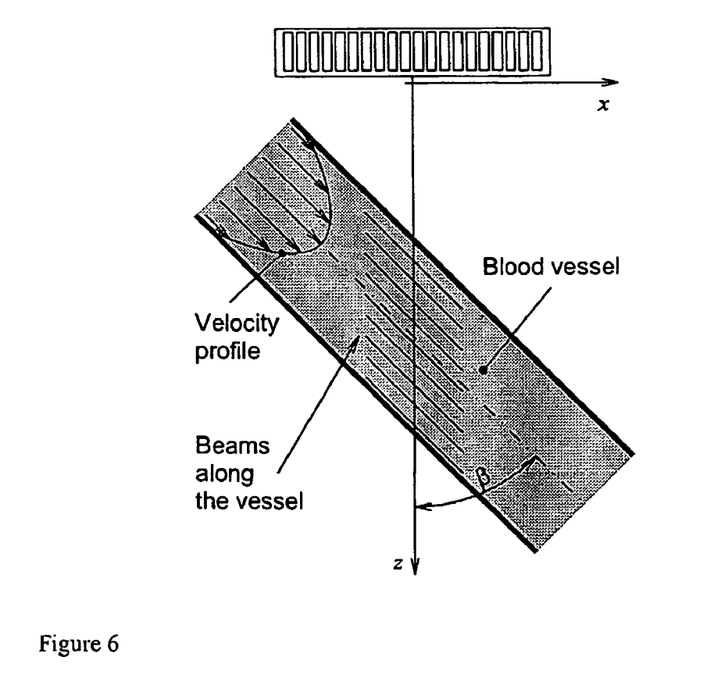
FIG. 6 shows the data used to find the velocity is taken from lines along the vessel.

FIG. 6 shows the measurement principle. The beam is focused along lines parallel to the blood velocity vector in the vessel. Each of these lines from emission n is cross-correlated with the line from emission n+1. The offset of the peak of the cross-correlation function is a measure of the movement of the scatterers. The traditional cross-correlation approach traces the signals towards and away from the transducer. Therefore only the axial velocity components can be found. With this method the signal is traced along the blood vessel, and velocity components parallel to the transducer surface can be measured. In the initial work [21] a broad beam was sent in the tissue and in receive the delays were set to focus along the axis of the vessel. The method has two problems: (1) it is not equally sensitive in the axial and lateral directions, and (2) the beam profile changes as a function of space, thus affecting the accuracy of the estimates. The latter of the problems was addressed by Jensen and Gori [23] by using matched filters. The filters have different impulse responses depending on the varying spatial impulse response (which can be numerically found), thus compensating for the fixed focus in transmit. This approach can be extended to synthetic aperture imaging in a straightforward manner.

The beams are perfectly focused in transmit and receive modes. A lateral translation of the scatterer causes a lateral translation of the low-resolution image. If one considers a laminar flow, then all the scatterers located at a radial distance r from the center of the vessel move with a constant velocity v. The distance, which they travel for the time Tprf between every two emissions, is $$\Delta l = |\vec{v}| T_{prf} \quad (22)$$

A line $s^{(n)}$ (l) at emission n is a shifted version of the line $s^{(n-N)}$ (l):

$$s^{(n)}(l) = s^{(n)}(l - \Delta l) \quad (23)$$

Cross-correlation of the two lines gives:

$$R_{1N}(\tau) = R_{11}(\tau - \Delta l) \quad (24)$$

where $R_{11}$ is the auto-correlation function of the signal, and $\tau$ is a lag in space. The velocity is then:

$$\hat{v} = \frac{\Delta l}{NT_{prf}} \quad (25)$$

The minimum detectable velocity is dependent on the spacing between the samples comprising the scan line s(t).

Another approach for finding the transverse velocity is to introduce a spatially oscillating beam transverse to the ultrasound beam as suggested in [24, 25]. The transverse spatial oscillation of the field can be generated by a single array transducer by special beam forming during transmit and/or receive. A sinusoidal pulse is emitted axially and properly apodized and phased during transmit and receive. Using, e.g., a non-focused emit beam and two sinc(sin(x)/x) functions for apodization in which different array elements have different vibration amplitudes along with plane wave focusing in receive beam forming give a field oscillating spatially in the transverse direction. Using the synthetic aperture technique makes it possible to obtain a spatially oscillating field for all depths, as it is the receive beam forming that essentially generates the spatial oscillation. The data is the employed in a modified auto-correlation estimator to find the velocity vector [26].

Velocity Estimation Using Speckle Tracking

Estimating the blood velocities by tracking the speckle pattern produced by moving blood has been suggested by Trahey and colleagues in 1987 [27, 28]. The idea is that the current random distribution of blood cells creates certain speckle patterns (two dimensional image). For the distance that the blood cells travel for the time of a few (usually 5 to 10) emissions these patterns remain intact and the change in their position can be traced by using a two dimensional convolution. The two-dimensional cross-correlation procedure has been simplified in subsequent papers [29], and made more robust by tracking the speckle pattern within smaller regions and using parallel beam forming [30, 31, 32].

Figure 7:
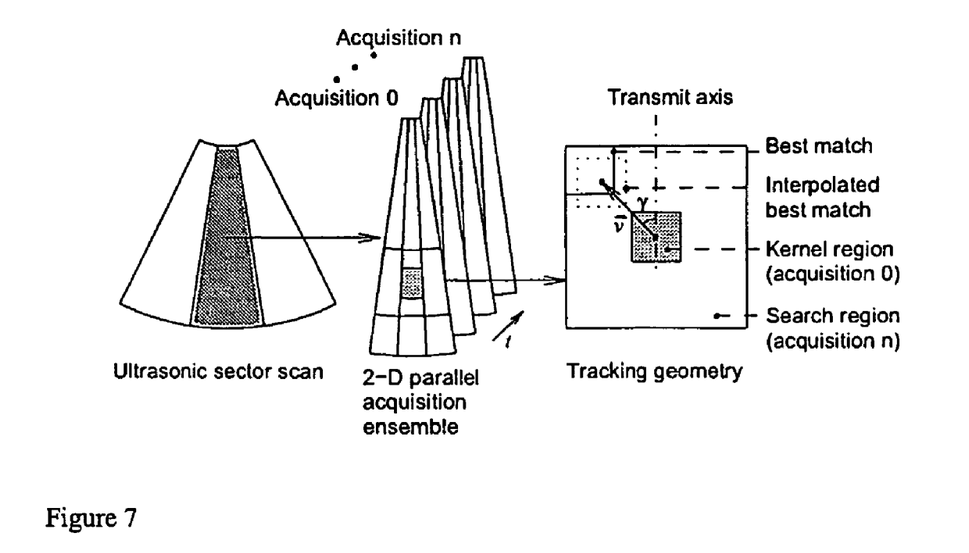
FIG. 7 shows 2D vector velocity estimation using speckle tracking (ensemble tracking).

The velocity estimation using speckle tracking (in the recent papers called "ensemble tracking" [32]) is illustrated in FIG. 7. Several acquisitions are done in the same direction. In receive several lines within the boundaries of the transmit beam are formed in parallel. To improve the performance the RF data from the receive beams are rescaled to compensate for the lateral transmit beam profile. A small 2D kernel is chosen and a match for it is sought in a larger bounding 2D region. The pattern-matching algorithm that was used in [32] is based on the so-called sum absolute difference (SAD) [29]:

$$\varepsilon(\eta, \xi, n) = \sum_{i=1}^{l} \sum_{j=1}^{k} |B_0(i, j)| - |B_n(i+\eta, j+\xi)| \quad (26)$$

where $\epsilon$ is the SAD coefficient, n is the acquisition number, $B_n(i,j)$ is the brightness of the pixel at location (i,j) in the nth image, l is the lateral dimension of the kernel in pixels, k is the axial dimension of the kernel in pixels, and $\eta$ and $\xi$ are lateral and axial pixel offsets of a prospective matching region within the search region. The best match is found at the smallest value of the difference. The result of the process is interpolated in a fashion similar to (21), and the interpolated offsets $(\hat{\eta}_m, \hat{\xi}_m)$ at which the maximum occurs are found. The magnitude of the velocity is given by:

$$|\vec{v}| = \frac{\sqrt{(\hat{\eta}_m \Delta x)^2 + (\hat{\xi}_m \Delta z)^2}}{nT_{prf}} \quad (27)$$

$$\gamma = \arctan \frac{\hat{\eta}_m \Delta x}{\hat{\xi}_m \Delta z}$$

where $\gamma$ is the angle between the beam axis and the velocity vector, $\Delta x$ and $\Delta z$ are the lateral and axial spatial sampling intervals respectively, and $T_{prf}$ is the pulse repetition interval. The matching can also be done with a full correlation search.

This approach can be modified for use with synthetic aperture imaging in the same way as the cross-correlation velocity estimators. The speckle patterns from emissions 0 and N, 1 and N+1, . . . , N−1 and 2N−1 can be tracked and then the estimates can be averaged for higher accuracy.

DESCRIPTION OF THE PREFERRED EMBODIMENT

Figure 8:
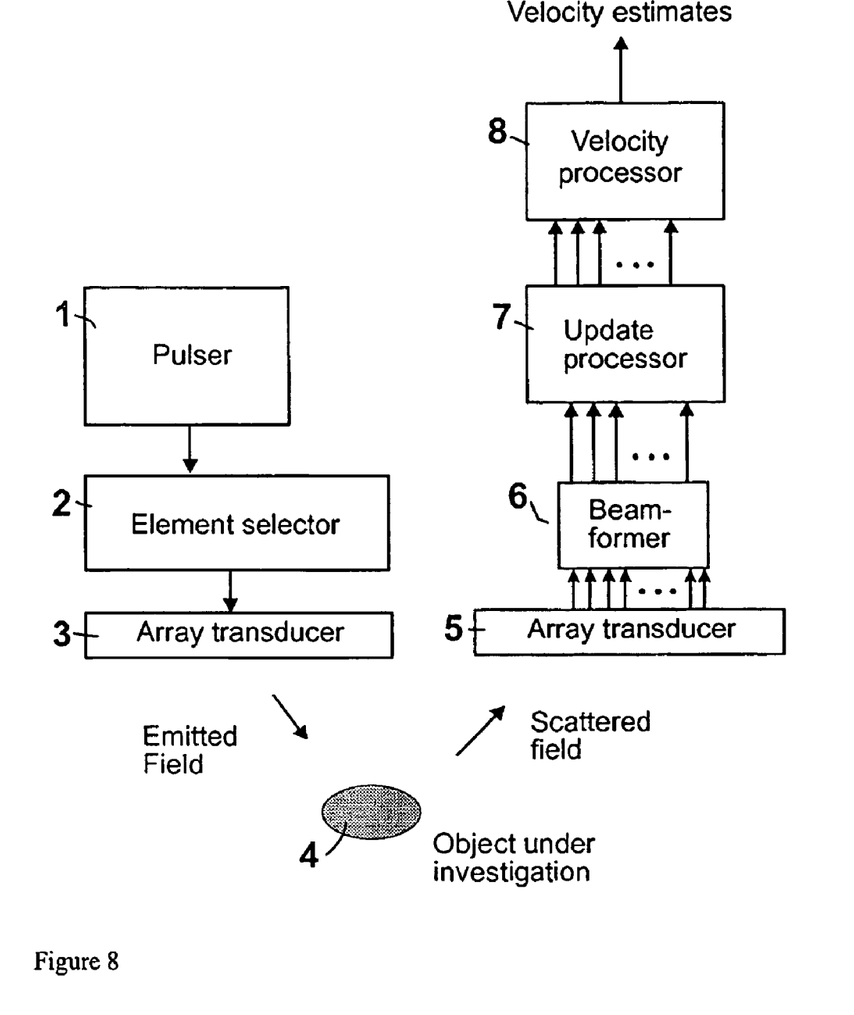
FIG. 8 shows a schematic block diagram of the main components of the system.

In FIG. 8 is shown an example of a preferred embodiment of an apparatus according to the invention. This embodiment of the invention has its application within diagnostic medical ultrasound. A typical example is visualization of the organs in the human body and determination of their blood flow.

In FIG. 8 the specific setup of the measuring apparatus itself is indicated schematically. It comprises a generator or pulser 1, an emit beam former 2 for selecting the transmission elements, a linear array ultrasound emitting transducer 3, a linear array ultrasound receiving transducer 5, a receive beam former 6 receiving signals from the receiving transducer 5, an update processor 7 for recursively updating the images, and an estimator processor 8 for estimating the velocity.

The pulser 1 generates a pulsed voltage signal with sinusoidal oscillations at a frequency of 3 MHz in each pulse, that is fed to the emit beam former 2. The emit beam former 2 splits up the signal from the pulser into a plurality of signals which are being fed to one or more of the respective elements of the emitting transducer array 3. The emit beam former 2 is capable of individually attenuating and delaying the signals to each or some of the elements of the transducer array 3. The ultrasound is then reflected by the object 4 and received by the elements of the transducer array 5. All of theses signals are then combined to focus all of the beams in the image in both transmit and receive in the beam processor 6 and the simultaneously focused signals are used for updating the image in the processor 7. The updated signals are used in the velocity estimation processor 8 to correlate the individual measurements to obtain the displacement between high-resolution images and thereby determine the velocity.

In the preferred embodiment the same linear array transducer is used for both emitting and receiving the pulsed ultrasound field. It consists of 64 elements with an element width of 0.26 mm and a spacing between neighboring elements of 0.03 mm. The height of the elements is 10 mm.

In the preferred embodiment individual elements are pulsed consecutively and the received signals are measured on all the elements of the transducer. The ultrasound beams are then focused in both transmit and receive in all directions of the image. After each emission the old information from the previous emission with the element is subtracted and the new information added. The image is thereby continuously updated.

Figure 9:
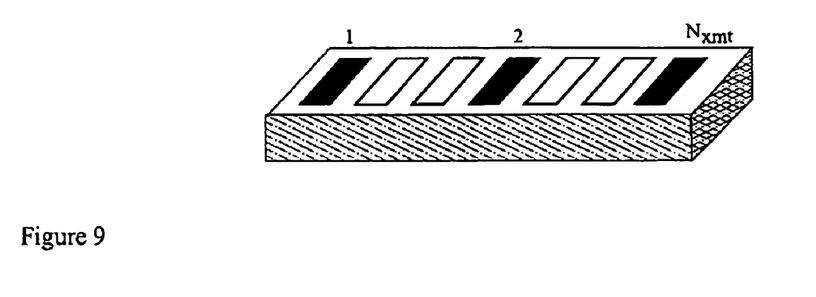
FIG. 9 shows the relation between the number of the skipped elements between two emissions and number of emissions. On this figure a linear array with 7 transducer elements is shown. The number of elements that are skipped is 2, indicating 3 emissions.

The elements are always used in transmit in the same order. For instance in FIG. 9 this means that the emission order in time is 1, 4, 7, 1, 4, 7,. This is necessary when recursive focusing is used for imaging, because it involves subtracting the information from the previous emission. Another parameter given on the figures is "Number of skipped elements". It indicates how many emissions are made before the same element is used again. The relation between these parameters are given in FIG. 9.

In order to increase the penetration depth and the signal-to-noise ratio, more than one element can be used during transmission. The idea is to send a spherical wave with eleven elements. A Hanning window can be applied on the amplitudes of the sending elements.

After every emission a high-resolution image is formed by summing the last N low-resolution images:

$$H^{(n)}(t) = \sum_{i=n-N+1}^{n} L^{(i)}(t) \quad (28)$$

where t is the time from the start of the emission. If the tissue is motionless, then $L^{(i)}(t) \equiv L^{(i-N)}(t)$ and $H^{(n)}(t) \equiv H^{(n-N)}(t)$. In the presence of motion, however, $L^{(n)}(t) \equiv L^{(n-N)}(t-2(N\Delta z)/c)$, where c is the speed of sound. If the velocity is constant, then:

$$H^{(n)}(t) = H^{(n-N)}\left(t - 2\frac{Nv_z T_{prf}}{c}\right) \quad (29)$$

where $T_{prf} = 1/f_{prf}$ is the pulse repetition period, and $v_z$ is the component of the velocity towards the transducer. This shift can be estimated using cross-correlation of the high-resolution lines $H^{(n)}(t)$ and $H^{(n-N)}(t)$, which are formed in the same direction of the image as shown in FIG. 5.

The cross-correlation becomes:

$$R_{n-N,n}(\tau) = \frac{1}{2T} \int_T H^{(n-N)}(t) H^{(n)}(t+\tau) dt \quad (30)$$

-continued $$= \frac{1}{2T}\int_T H^{(n-N)}(t)H^{(n-N)}(t+\tau)dt$$

$$= R_{n-N,n-N}(\tau - t_s)$$

where $$t_s = 2\frac{Nv_z T_{prf}}{c}$$

is the time shift due to motion. The peak of the cross-correlation function is located at $\tau = t_s$. The velocity can be found from the time shift:

$$v_z = \frac{c}{2}\frac{t_s}{NT_{prf}} \quad (31)$$

The lines at emissions $n-i$ and $n-N-i$ are subject to the same time shift:

$$R_{n-N-i,n-i} = R_{N-n-i,N-n-i}(\tau - t_s) \quad (32)$$

and the peak of their cross-correlation function is also located at a lag $\tau = t_s$, as shown in FIG. 5. The estimate of the cross-correlation function $R_{n-N-i, n-i}(\tau)$ can be therefore be improved by averaging over several emissions i.

The velocity of blood changes as a function of space and time in the human body. To estimate the velocity at the different spatial positions, each of the RF lines is divided into a number of segments as shown in FIG. 5. A cross-correlation function is estimated for each of the segments. Normally the signals are digital, and therefore the discrete version of the cross-correlation becomes:

$$\hat{R}_{n-N,n}[\eta, i_{seg}] = \frac{1}{N_s}\sum_{k=(i_{seg}-1)N_s}^{i_{seg}N_s - 1} H^{(n-N)}[k]H^{(n)}[k+\eta] \quad (33)$$

where $N_s$ is the number of samples in a segment and $i_{seg}$ is the number of the segment. If the velocity does not change significantly for several sequential acquisitions $N_c$, then the estimate can be improved by averaging the estimated cross-correlation functions:

$$\hat{R}_{1Nd}[\eta, i_{seg}] = \frac{1}{N_c}\sum \hat{R}_{n-1-N,n-1}[\eta, i_{seg}] \quad (34)$$

FIG. 5 shows the case for which $N_c = N$. If the images were created after every N emissions, then the total number of emissions needed for the velocity estimate would be $N_c N$. For $N=8$ and $N_c=16$, the total number of emissions would be $N_c N=128$. The correlation between the high-resolution lines would decrease due to acceleration, velocity gradients and migration of scatterers. In the new approach only $N+N_c=24$ emissions are necessary, thus, preserving the high-correlation between the images and giving the possibility of estimating the flow with low bias and variance.

The lag at which the maximum occurs is $\eta_6$ m. The estimated velocity is then:

$$\hat{v}_z = \frac{c}{2}\frac{\eta_m f_{prf}}{Nf_s} \quad (35)$$

The precision of the estimate can be improved by fitting a second order curve to the correlation function, and thereby interpolate the time shift:

$$\eta_s = \eta_m - \frac{\hat{R}_{1Nd}[\eta_m + 1] - \hat{R}_{1Nd}[\eta_m - 1]}{2(\hat{R}_{1Nd}[\eta_m + 1] - 2\hat{R}_{1Nd}[\eta_m] + \hat{R}_{1Nd}[\eta_m - 1])} \quad (36)$$

Stationary echo canceling is done prior to correlation on the images that were obtained at every Nth emission, i.e. between images n and n−kN, where k ∈ Z.

REFERENCES

[1] J. T. Ylitalo. In-vitro study of computed ultrasound imaging method. In Proc. IEEE Ultrason. Symp., pages 1577-1580, 1994.

[2] J. T. Ylitalo and H. Ermert. Ultrasound synthetic aperture imaging: monostatic approach. IEEE Trans. Ultrason., Ferroelec., Freq. Contr., 41:333-339, 1994.

[3] J. T. Ylitalo. Synthetic aperture ultrasound imaging using a convex array. In Proc. IEEE Ultrason. Symp., pages 1337-1340, 1995.

[4] J. T. Ylitalo. A fast ultrasonic synthetic aperture imaging method: application to NDT. Ultrasonics, pages 331-333, 1996.

[5] J. T. Ylitalo. On the signal-to-noise ratio of a synthetic aperture ultrasound imaging method. Eur. J. Ultrasound, pages 277-281, 1996.

[6] M. Karaman, P. C. Li, and M. O'Donnell. Synthetic aperture imaging for small scale systems. IEEE Trans. Ultrason., Ferroelec., Freq. Contr., 42:429-442, 1995.

[7] R. Y. Chiao and L. J. Thomas. Analytic evaluation of sampled aperture ultrasonic imaging techniques for NDE. IEEE Trans. Ultrason., Ferroelec., Freq. Contr., 41:484-493, 1994.

[8] S. Holm and H. Yao. Improved framerate with synthetic transmit aperture imaging using prefocused subapertures. Proc. IEEE Ultrason. Symp., pages 1535-1538, 1997.

[9] G. R. Lockwood, J. R. Talman, and S. S. Brunke. Real-time 3-D ultrasound imaging using sparse synthetic aperture beamforming. IEEE Trans. Ultrason., Ferroelec., Freq. Contr., 45:980-988, 1998.

[10] C. R. Hazard and G. R. Lockwood. Theoretical assessment of a synthetic aperture beamformer for real-time 3-D imaging. IEEE Trans. Ultrason., Ferroelec., Freq. Contr., 46:972-980, 1999.

[11] S. I. Nikolov, K. Gammelmark, and J. A. Jensen. Recursive ultrasound imaging. Proc. IEEE Ultrason. Symp., volume 2, pages 1621-1625, 1999.

[12] L. F. Nock and G. E. Trahey. Synthetic receive aperture imaging with phase correction for motion and for tissue inhomogenities—part II: effects of and correction for motion. IEEE Trans. Ultrason., Ferroelec., Freq. Contr., 39:496-501, 1992.

[13] H. S. Bilge, M. Karaman, and M. O'Donnell. Motion estimation using common spatial frequencies in synthetic aperture imaging. In Proc. IEEE Ultrason. Symp., pages 1551-1554, 1996.

[14] S. G. Foster, P. M. Embree, and W. D. O'Brien. Flow velocity profile via time-domain correlation: Error analysis and computer simulation. IEEE Trans. Ultrason., Ferroelec., Freq. Contr., 37:164-175, 1990.

[15] S. I. Nikolov, K. Gammelmark, and J. A. Jensen. Velocity estimation using recursive ultrasound imaging and spatially encoded signals. In Proc. IEEE Ultrason. Symp., volume 2, pages 1473-1477, 2000.

[16] J. A. Jensen. Estimation of Blood Velocities Using Ultrasound: A Signal Processing Approach. Cambridge University Press, New York, 1996.

[17] J. A. Jensen. Stationary echo canceling in velocity estimation by time-domain cross-correlation. IEEE Trans. Med. Imag., 12:471-477, 1993b.

[18] C. Kasai, K. Namekawa, A. Koyano, and R. Omoto. Real-time two-dimensional blood flow imaging using an autocorrelation technique. IEEE Trans. Son. Ultrason., 32:458-463, 1985.

[19] K. W. Ferrara and V. R. Algazi. Estimation of blood velocity using the wideband maximum likelihood estimator. Proc. IEEE Ultrason. Symp., pages 897-901, 1989.

[20] O. Bonnefous. Measurement of the complete 3D velocity vector of blood flows. Proc. IEEE Ultrason. Symp., pages 795-799, 1988.

[21] J. A. Jensen and I. R. Lacasa. Estimation of blood velocity vectors using transverse ultrasound beam focusing and cross-correlation. Proc. IEEE Ultrason. Symp., pages 1493-1497, 1999.

[22] I. R. Lacasa. Estimation of blood velocities with ultrasound. Master's thesis, Department of Information Technology, Technical University of Denmark, 1999.

[23] J. A. Jensen and P. Gori. Improved accuracy in the estimation of blood velocity vectors using matched filtering. Proc. IEEE Ultrason. Symp., volume 2, pages 1525-1530, 2000.

[24] P. Munk. Estimation of blood velocity vectors using ultrasound. PhD thesis, Department of Information Technology, Technical University of Denmark, Lyngby, Denmark, 2000.

[25] J. A. Jensen and P. Munk. A new method for estimation of velocity vectors. IEEE Trans. Ultrason., Ferroelec., Freq. Contr., 45:837-851, 1998.

[26] J. A. Jensen. A new estimator for vector velocity estimation. IEEE Trans. Ultrason., Ferroelec., Freq. Contr., 48(4): 886-894, 2001.

[27] G. E. Trahey, J. W. Allison, and O. T. von Ramm. Angle independent ultrasonic detection of blood flow. IEEE Trans. Biomed. Eng., BME-34:965-967, 1987.

[28] G. E. Trahey, S. M. Hubbard, and O. T. von Ramm. Angle independent ultrasonic blood flow detection by frame-to-frame correlation of B-mode images. Ultrasonics, 26:271-276, 1988.

[29] L. N. Bohs and G. E. Trahey. A novel method for angle independent ultrasonic imaging of blood flow and tissue motion. IEEE Trans. Biomed. Eng., 38:280-286, 1991.

[30] L. N. Bohs, B. J. Geiman, K. R. Nightingale, C. D. Choi, B. H. Friemel, and G. E. Trahey. Ensemble tracking: a new method for 2D vector velocity measurement. Proc. IEEE Ultrason. Symp., pages 1485-1488, 1995.

[31] B. Geiman, L. Bohs, M. Anderson, and G. E. Trahey. Initial experimental results using ensemble tracking for 2D vector velocity measurement. Proc. IEEE Ultrason. Symp., pages 1241-1244, 1996.

[32] L. N. Bohs, B. J. Geiman, S. M. Breit, and G. E. Trahey. Ensemble tracking for 2D vector velocity measurement: experimental and initial clinical results. IEEE Trans. Ultrason., Ferroelec., Freq. Contr., 45:912-924, 1998.

The invention claimed is:

1. An apparatus for measuring the velocity of a moving object or the velocities of a collection of moving objects, the apparatus comprising:

a generator for generating excitation signals;

an emitting multi-element transducer for transforming the excitation signals into wave energy by emitting the wave energy by excitation of elements or groups of elements of the multi-element transducer in a predefined sequence;

a receiving transducer having a plurality of receiving transducer elements for receiving signals from the moving object or objects generated by interaction with the wave energy emitted from the emitting multi-element transducer;

a receive beam former for receiving signals from the plurality of receiving transducer elements and for delaying each of the signals from the plurality of receiving transducer elements individually relative to the others of the signals from the plurality of receiving transducer elements;

an update processor for obtaining a set of focused beams for respective excitations of the elements; and a velocity processor executing computer-readable instructions for directing the velocity estimator to:

form a first image from a first set of focused beams, where the first set of focused beams are acquired in response to excitation of respective sets of elements of the multi-element transducer, and where the sets of elements are excited in a first predetermined order;

form a second image from a second set of focused beams, where the second set of focused beams are acquired in response to excitation of respective sets of elements of the multi-element transducer, and where the sets of elements are excited in a second predetermined order, where the first predetermined order and the second predetermined order are the same order; and determine the velocity or velocities by correlating the first image and the second image.

2. An apparatus according to claim 1, wherein the update processor updates the first and second sets of focused beams after each emission of energy according to:

$$H_l^{(n-1)}(t) = \sum_{m=(n-N_{xmt})}^{n-1} a_{k(m)} \cdot L_{lk(m)}^{(m)}(t)$$

$$H_l^{(n)}(t) = \sum_{m=(n-N_{xmt}+1)}^{n} a_{k(m)} \cdot L_{lk(m)}^{(m)}(t)$$

$$H_l^{(n)} = H_l^{(n-1)} + a_{k(n)} \cdot L_{lk(n)}^{(n)}(t) - a_{k(n-N_{xmt})} \cdot L_{lk(n-N_{xmt})}^{(n-N_{xmt})}(t)$$

where $$L_{lk}^{(n)}$$

is the beam formed signal at emission n with element k for image line I, $a_{k(m)}$ is a weighting coefficient, and $N_{xmt}$ is the number of transmissions between two emissions with the same element.

3. An apparatus according to claim 1 wherein the emitting multi-element transducer transforms the excitation signals into sound energy.

4. An apparatus according to claim 1 wherein the emitting multi-element transducer transforms the excitation signals into ultrasound energy.

5. An apparatus according to claim 1 wherein the emitting multi-element transducer transforms the excitation signals into electromagnetic energy.

6. An apparatus according to claim 1 wherein the elements of the emitting multi-element transducer emit the wave enemy by excitation of a number of elements at the same time during transmission.

7. An apparatus according to claim 1 wherein the velocity processor uses a cross-correlation between the sets of focused beams.

8. An apparatus according to claim 7 wherein the velocity processor averages the cross-correlation over a number of pulse emissions.

9. An apparatus according to claim 1 wherein the velocity processor uses a maximum likelihood estimator on the sets of focused beams.

10. An apparatus according to claim 1 wherein the velocity processor uses an autocorrelation on samples from the sets of focused beam signals.

11. An apparatus according to claim 1 wherein the velocity processor uses a correlation between the speckle patterns of two beam formed images consisting of a number of beams.

12. An apparatus according to claim 1 wherein the emitting multi-element transducer and the receiving transducer have respective sensitivities which in combination give a focused sensitivity in a direction along a velocity vector of the moving object.

13. An apparatus according to claim 1 wherein the emitting multi-element transducer and the receiving transducer have respective sensitivities which in combination give a resulting sensitivity oscillating spatially in a direction transverse to the set of focused beams.

14. A method of measuring the velocity of a moving object or the velocities of a collection of moving objects, the method comprising the steps of:
generating a plurality of excitation signals;
transforming, using N groups of elements of a multi-element transducer, the plurality of excitation signals into a plurality of wave energy pulses by excitation of the N groups of elements in a predefined sequence;
emitting the plurality of wave energy pulses in a direction towards the moving object or collection of moving objects;
receiving, using a receiving transducer with a plurality of receiving transducer elements, echo signals from the moving object or objects generated by interaction with the wave energy emitted from the emitting transducer, the plurality of receiving elements each outputting a signal corresponding to a received echo signal;
outputting, from the plurality of receiving transducer elements, beam forming signals and delaying each of the beam forming signals output from the plurality of receiving transducer elements individually relative to each other;
obtaining a set of focused beams for every pulse emission;
forming a first image by selecting a first set of focused beams acquired in response to excitation of respective sets of elements of the multi-element transducer, where elements are excited in a first predetermined order;
forming a second image by selecting a second set of focused beams acquired in response to excitation of respective sets of elements of the multi-element transducer, and where the sets of elements are excited in a second predetermined order, where the first predetermined order and the second predetermined order are the same order; and
determining the velocity or velocities by correlating the first image and the second image.

15. A method according to claim 14, wherein the first and second sets of focused beams are updated after each emission of energy according to:

$$H_l^{(n-1)}(t) = \sum_{m=(n-N_{xmt})}^{n-1} a_{k(m)} \cdot L_{lk(m)}^{(m)}(t)$$

$$H_l^{(n)}(t) = \sum_{m=(n-N_{xmt}+1)}^{n} a_{k(m)} \cdot L_{lk(m)}^{(m)}(t)$$

$$H_l^{(n)} = H_l^{(n-1)} + a_{k(n)} \cdot L_{lk(n)}^{(n)}(t) - a_{k(n-N_{xmt})} \cdot L_{lk(n-N_{xmt})}^{(n-N_{xmt})}(t)$$

where $$L_{lk}^{(n)}$$

is the beam formed signal at emission n with element k for image line I, $a_{k(m)}$ is a weighting coefficient, and $N_{xmt}$ is the number of transmissions between two emissions with the same element.

* * * * *

UNITED STATES PATENT AND TRADEMARK OFFICE
CERTIFICATE OF CORRECTION

PATENT NO. : 7,542,790 B2 Page 1 of 1
APPLICATION NO. : 10/491170
DATED : June 2, 2009
INVENTOR(S) : Jørgen Arendt Jensen

It is certified that error appears in the above-identified patent and that said Letters Patent is hereby corrected as shown below:

Title page, item (73), ("Assignee"), "Gentoft (DK)" should read --Gentofte (DK)--.

Title page, item (57), ("ABSTRACT"), line 16,
"The estimation processor (8) to correlate the" should read
--The update signals are used in the velocity estimation processor (8) to correlate the--.

Signed and Sealed this

Eighth Day of December, 2009

David J. Kappos
*Director of the United States Patent and Trademark Office*